United States Patent [19]

Robertson et al.

[11] Patent Number: 5,860,581
[45] Date of Patent: Jan. 19, 1999

[54] ANVIL FOR CIRCULAR STAPLER

[75] Inventors: John Charles Robertson, Bloomfield; Frank J. Viola, Sandy Hook, both of Conn.

[73] Assignee: United States Surgical Corporation, Norwalk, Conn.

[21] Appl. No.: 758,104

[22] Filed: Nov. 29, 1996

Related U.S. Application Data

[63] Continuation of Ser. No. 217,264, Mar. 24, 1994, abandoned.

[51] Int. Cl.[6] ............................ A61B 17/115; A61B 17/04
[52] U.S. Cl. ..................... 227/179.1; 227/19; 227/180.1
[58] Field of Search ............................... 227/175.1, 178.1, 227/179.1, 180.1, 19

[56] References Cited

U.S. PATENT DOCUMENTS

| | | |
|---|---|---|
| 4,304,236 | 12/1981 | Conta et al. . |
| 4,505,272 | 3/1985 | Utyamyshev et al. . |
| 4,752,024 | 6/1988 | Green et al. ............................ 227/19 |
| 4,903,697 | 2/1990 | Resnick et al. ......................... 227/19 |
| 5,104,025 | 4/1992 | Main et al. ............................ 227/175 |
| 5,119,983 | 6/1992 | Green et al. . |
| 5,205,459 | 4/1993 | Brinkerhoff et al. . |
| 5,275,322 | 1/1994 | Brinkerhoff et al. .................. 227/175 |
| 5,411,508 | 5/1995 | Bessler et al. ...................... 227/179.1 |

*Primary Examiner*—Rinaldi I. Rada
*Assistant Examiner*—Boyer Ashley

[57] ABSTRACT

An anvil assembly for use with a circular surgical stapler is disclosed. The anvil assembly includes an anvil body, an anvil disposed around the anvil body and engaged therewith, and a tether line having a first end connected to the anvil body and a second end connected to the anvil. The anvil assembly is configured so that upon completion of the stapling operation, the anvil is disengaged from the anvil body, rotated, and withdrawn from the patient via the tether line. A method of using the anvil assembly is also disclosed.

15 Claims, 9 Drawing Sheets

ANVIL FOR CIRCULAR STAPLER

This is a continuation of application Ser. No. 08/217,264 filed on Mar. 24, 1994, now abandoned.

BACKGROUND

1. Field of the Invention

This invention relates to an instrument and method for circular surgical stapling of hollow body organs, and more particularly, to an improved anvil assembly having a tether line for retrieving a disengaged anvil portion from the hollow body organ after stapling.

2. Description of the Prior Art

There are several known types of surgical staplers in which the stapling function takes place at a location which is relatively remote from the location at which the stapler is held and actuated by the operator. One example of such a stapler is the circular anastomosis surgical stapler shown illustratively in Conta et al. U.S. Pat. No. 4,304,236. Typically, in instruments of this type exemplified by this reference, tissue to be stapled is clamped between an anvil assembly and a staple holding assembly, both of which are located at the distal end of the instrument. The clamped tissue is stapled by driving one or more staples from the staple holding assembly so that the ends of the staples pass through the tissue and are clinched by contact with the anvil assembly. The forces required to operate the instrument are applied by the operator of the instrument to one or more actuator elements located at or near the proximal end of the instrument. The distal and proximal portions of the instrument are joined by a longitudinal connecting shaft structure along which the actuating forces and motions are transmitted to the distal operating elements.

In use in the typical application of joining two intestinal sections together, instruments of the type mentioned above are first positioned so that the staple holding assembly is inside the end of a first intestinal section and the anvil assembly is inside the end of a second intestinal section. The severed ends of the intestinal sections are typically secured by purse strings and then clamped between the staple holding assembly and the anvil assembly. The instrument is then operated so as to drive staples from the staple holding assembly through the clamped tissue, and against an anvil portion of the anvil assembly. The same operation of the instrument which drives the staples also drives a knife to cut away the waste or excess tissue inside the annular array of staples and thereby clear the lumen between the connected organ sections.

The joining of the intestinal sections now complete, the instrument can be removed. To remove the instrument from the stapled tissue, the anvil assembly is typically moved away from the staple holding assembly so that the tissue is no longer clamped by the instrument. The entire instrument is then pulled out of the first intestinal section.

In withdrawing the instrument, the anvil portion of the anvil assembly is withdrawn past the stapled tissue. Since the outer circumferential surface of the anvil has a diameter greater than that of the intestinal sections at the point where the intestinal sections have been recently stapled, the stapled tissue is stretched by the contact of the anvil with the stapled tissue. Reducing contact between the full circumference of the anvil and the stapled tissue, can decrease the degree of stretching of the newly stapled tissue.

In view of the foregoing, there is a need to provide an anvil assembly, and method of using same, which facilitates withdrawal of the anvil assembly from a hollow body organ. There is also a need for an anvil assembly which minimizes stretching of tissue upon withdrawal.

SUMMARY

An anvil assembly for use with a circular stapling device is provided in which the anvil assembly comprises a body portion, an anvil ring portion at least partially disengageable from the body portion for clinching staples, means for latching the anvil ring portion to the body portion, and means for linking the body portion to the anvil ring portion when the anvil ring portion is disengaged from the body portion.

In a preferred embodiment, the latching means is at least one male member defined by the anvil body and an anvil ring portion having a lower portion defining at least one recess configured to receive the male member. In addition, biasing means are provided to bias the male member into the recess. The biasing means can include a removable "knife ring" or "cut ring" configured for becoming integral with a knife blade after firing the instrument. Preferably, after the knife becomes frictionally engaged with the cut ring, retraction of the knife and cut ring removes the biasing force on the male member and unlatches the anvil ring.

In another preferred embodiment, the latching means is a corrugated spring band defining a plurality of male members. The biasing means is a removable knife ring configured for reception of a knife blade for the purpose of becoming integral with the knife blade.

In yet another preferred embodiment, the latching means is at least one tab member defined by the anvil body. The tab member is configured for placement into the recess, and further configured to be engaged by a knife blade for the purpose of removing the tab member from the recess to permit disengagement of the anvil ring portion from the anvil body.

In still another preferred embodiment, the latching means is a washer assembly having at least one washer. The washer has an upper portion, and a lower portion, the upper portion is configured for attachment to the anvil body, the lower portion forms at least one leg portion configured for placement into the recess.

In addition, in each of the above embodiments, the anvil linking means is preferably a tether line having a first end affixed to said anvil body portion, and a second end affixed to said anvil ring portion.

BRIEF DESCRIPTION OF THE DRAWINGS

Further features of the invention, its nature and various advantages will be more apparent from the following detailed description of preferred embodiments, and from the accompanying drawings, in which.

DETAILED DESCRIPTION OF PREFERRED EMBODIMENTS

Figure 1:
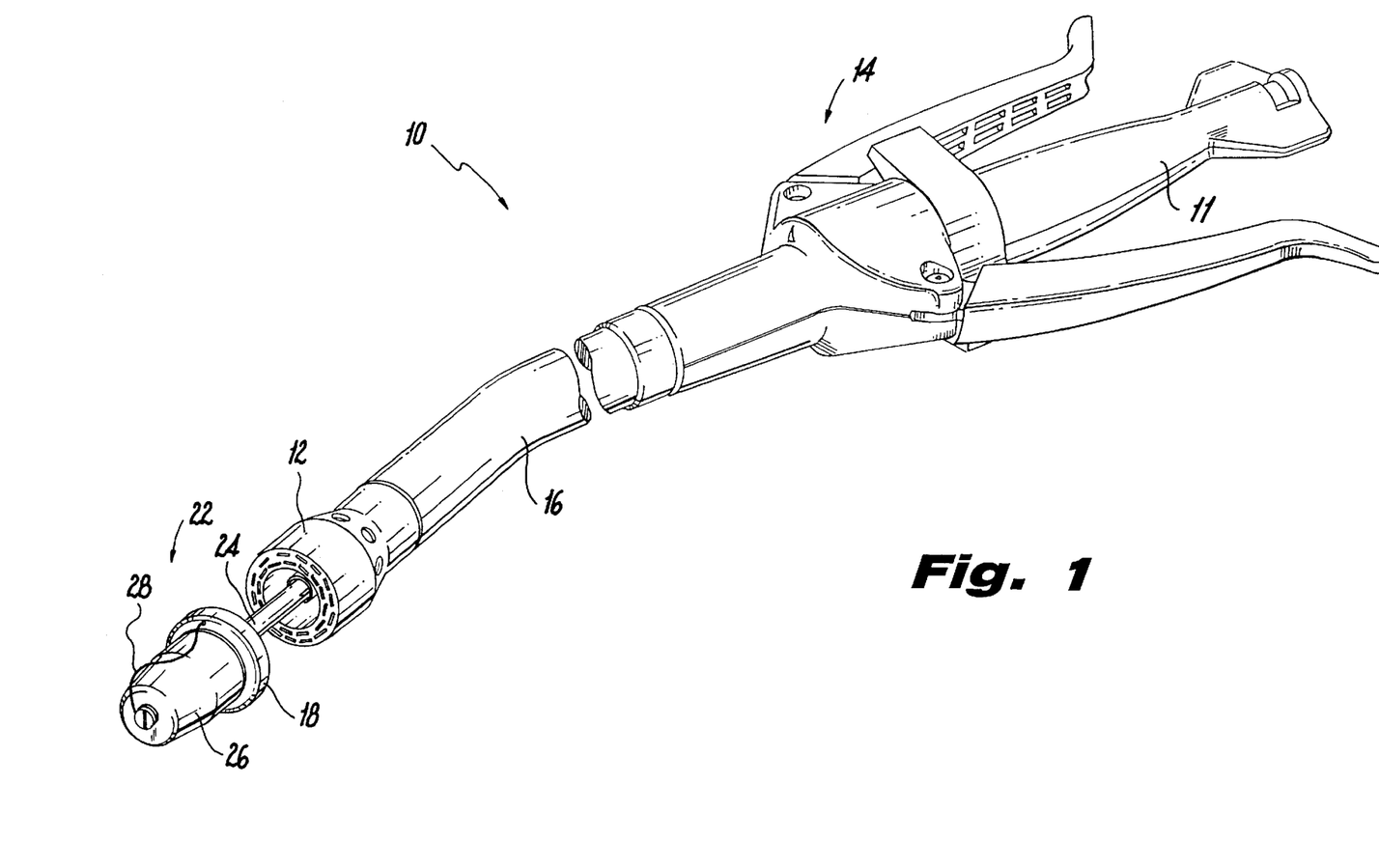
FIG. 1 is a perspective view of a circular stapling apparatus illustrating an anvil assembly of an embodiment of the present invention in an extended position.

Turning now to the drawings, in which like reference numerals describe similar or identical elements, FIG. 1 illustrates a circular anastomosis surgical stapler utilizing the anvil assembly of the present invention. A typical application of a circular anastomosis surgical stapler is connecting together two sections of hollow tubular body organ (e.g., two intestinal sections) by means of an annular array of staples which surrounds a lumen or passageway within the interiors of the connected organ sections. Circular surgical stapler 10 includes distal stapling assembly 12, proximal actuator assembly 14, and longitudinal shaft assembly 16 for connecting the distal and proximal assemblies and for transmitting actuating forces and motions from the actuator assembly to the stapling assembly. Commonly assigned U.S. Pat. No. 5,119,983 discloses a substantially similar circular stapler and is incorporated herein by reference. Anvil assembly 22, as best seen in FIG. 3, includes monolithically formed or integral anvil ring 18 which has a plurality of staple clinching grooves 20 for clinching staples driven from stapler assembly 12.

Figure 2:
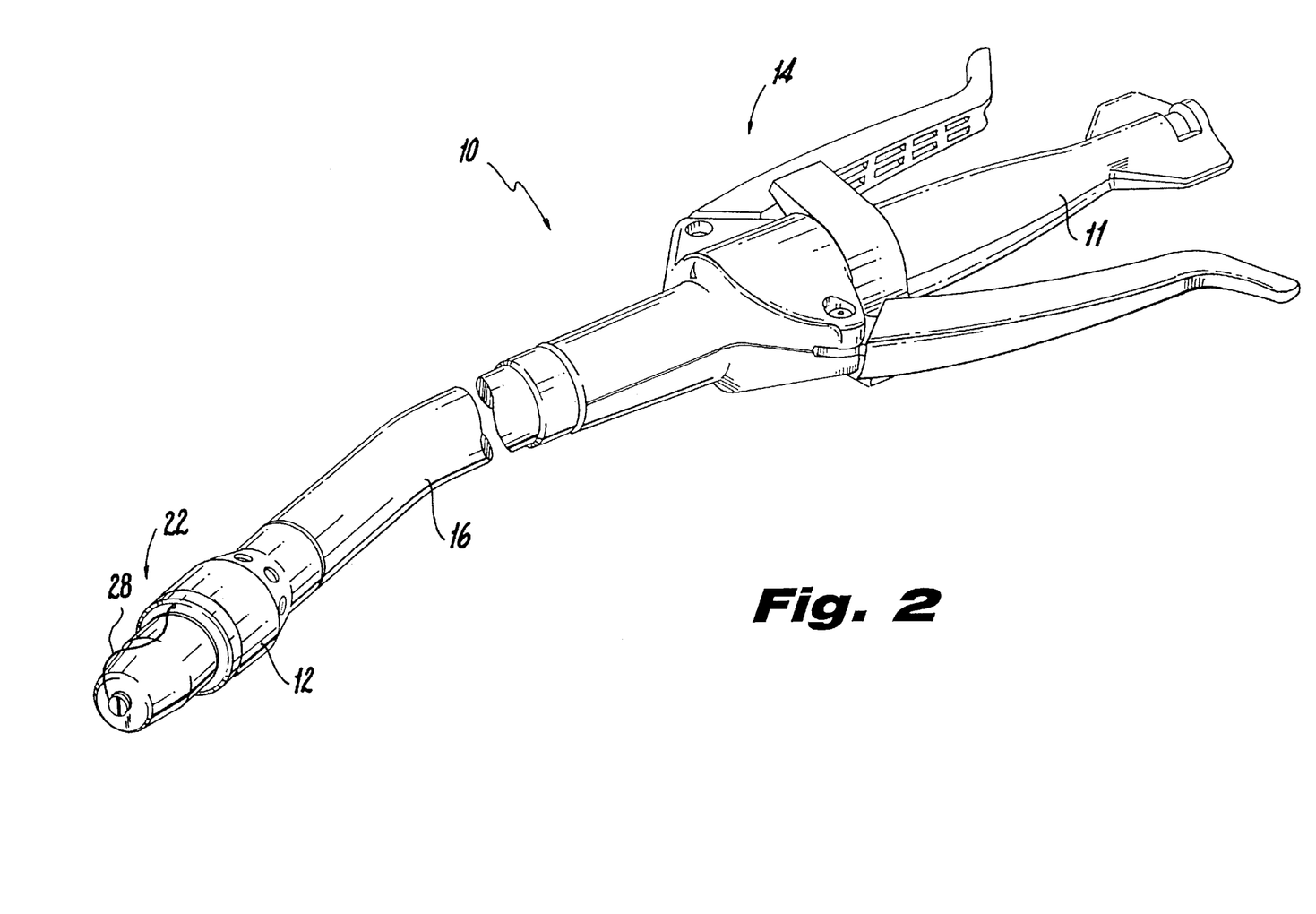
FIG. 2 is a view of the anvil assembly of FIG. 1 in a retracted position.
Figure 3:
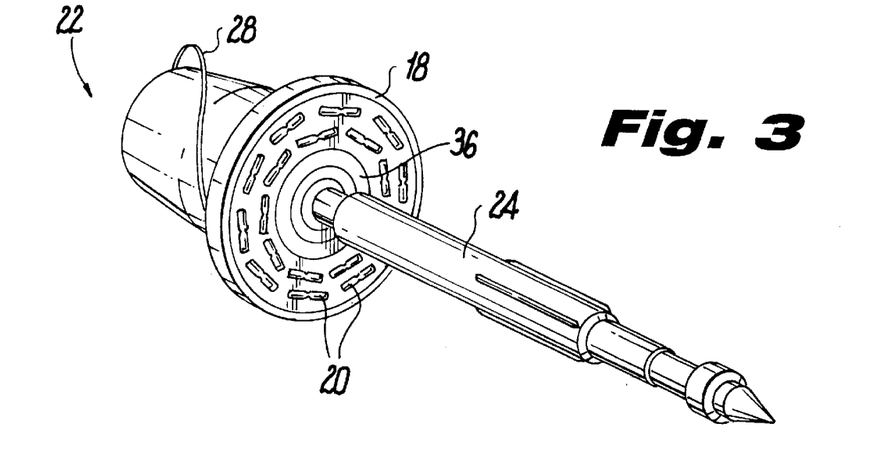
FIG. 3 is a proximal perspective view of a preferred embodiment of an anvil assembly of the present invention.

In accordance with one embodiment of the present invention, as seen in FIGS. 1–3, anvil assembly 22 is mounted on the distal end of anvil support member 24. The proximal end of member 24 is mountable to a movable shaft (not shown) at least partially disposed within assembly 16. As is known in the art, rotation of wing nut 11 causes longitudinal motion of the movable shaft and attached anvil assembly 22 relative to stapling assembly 12 so that space between opposing faces of anvil assembly 22 and stapling assembly 12 can be varied.

Figure 4:
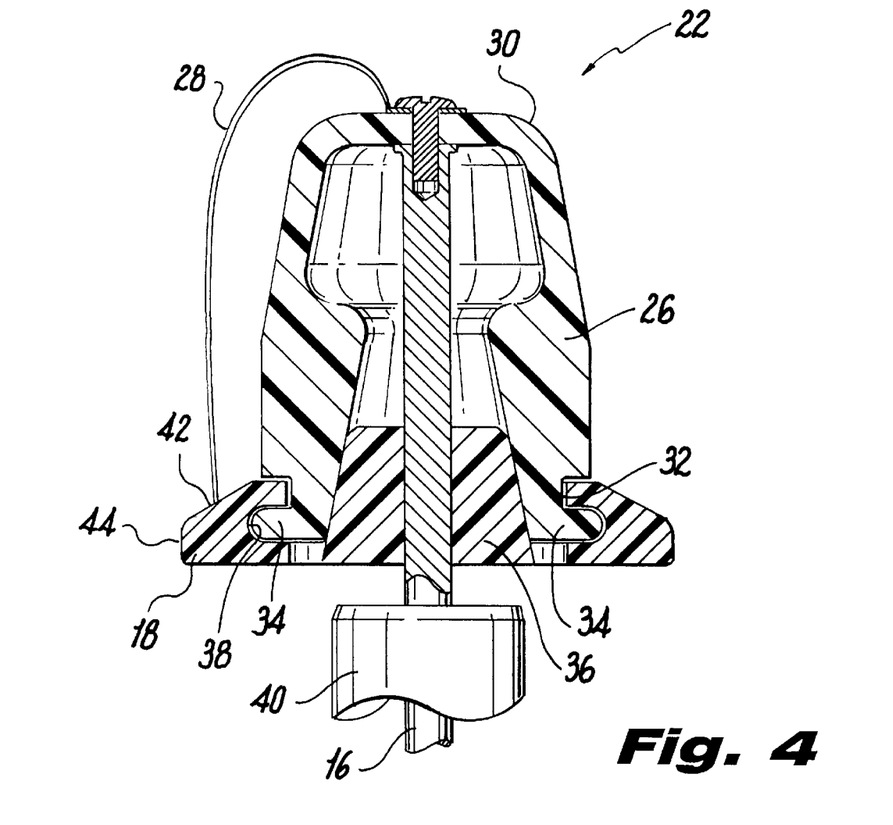
FIG. 4 is a cross sectional view of a preferred embodiment of an anvil assembly of the present invention.

Referring to FIG. 1, anvil assembly 22 includes a disengageable anvil ring 18 disposed around body portion 26 and linked with body portion 26 via tether line 28. In a preferred embodiment, as seen in FIG. 4, body portion 26 includes an upper body portion 30, and a lower body portion 32 forming tab members 34. Knife ring 36 is disposed within body portion 26 for providing biasing pressure against tab members 34 in an outward direction towards anvil ring 18. The biasing pressure forces tab members 34 into recesses 38 of anvil ring 18 thereby engaging anvil ring 18 with body portion 26. Knife blade 40 is mounted on the instrument for concentric movement over anvil support member 24 for reciprocal movement longitudinally along anvil support member 24 for the purpose of cutting tissue and contacting knife ring 36 so as to become embedded therein.

Figure 5:
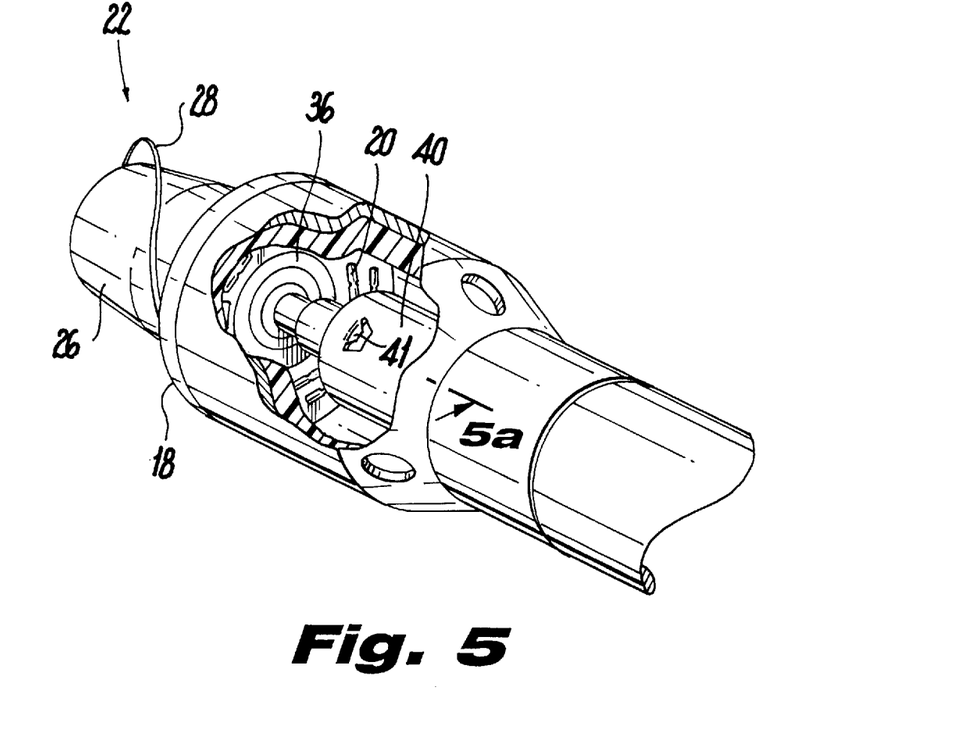
FIG. 5 is a perspective view in partial cutaway of a circular stapling instrument utilizing an embodiment of a preferred anvil assembly of the present invention in the fully loaded, unfired condition.
Figure 5A:
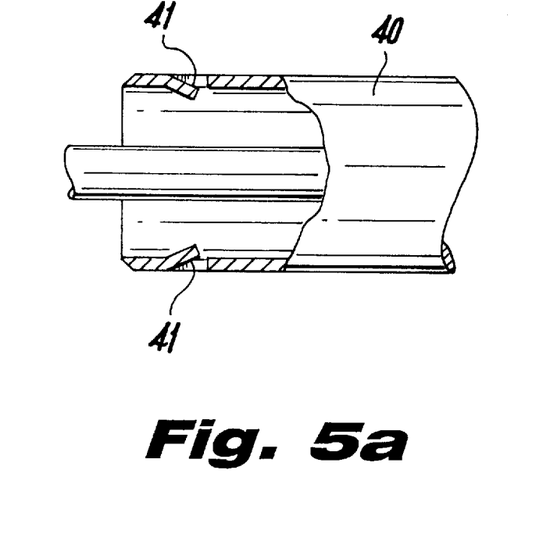
FIG. 5A is a side-elevational, cutaway view of the knife blade suitable for use with the present invention.
Figure 6:
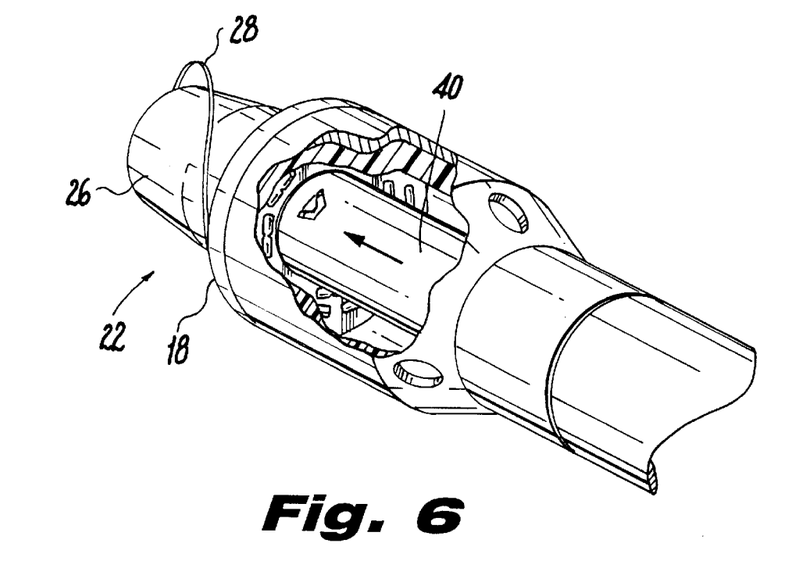
FIG. 6 is a view similar to FIG. 5 illustrating contact of a knife blade with an anvil assembly after firing of the staples.
Figure 7:
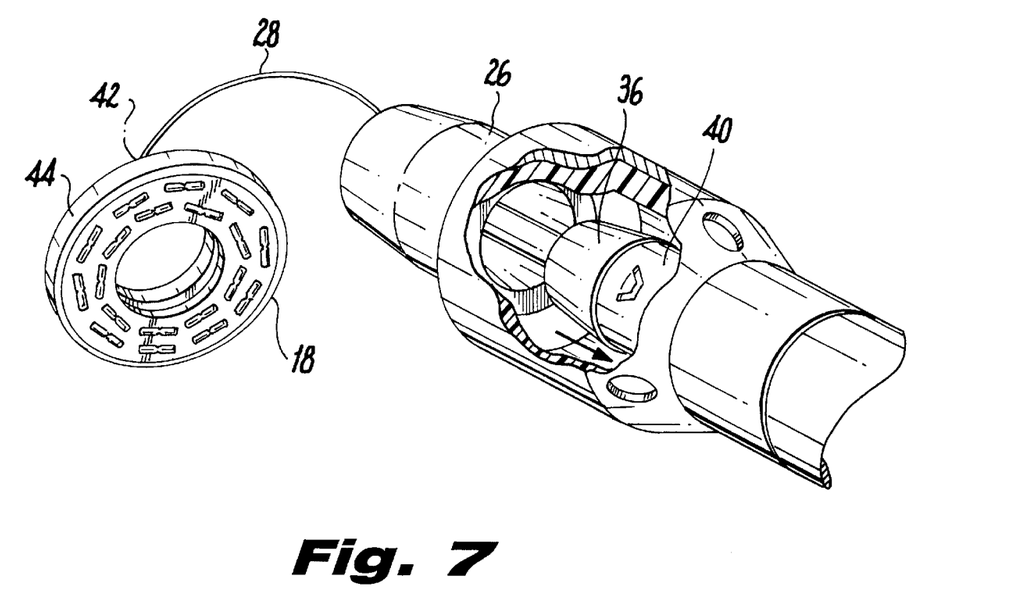
FIG. 7 is a view similar to FIG. 6 illustrating a preferred embodiment of an anvil assembly of the present invention with a disengaged anvil ring.

Referring to FIGS. 5–7, after the staples have been fired into the tissue (not shown for purposes of clarity) held between stapling assembly 12 and anvil assembly 22, knife blade 40 is directed distally into knife ring 36 as the actuator assembly 14 is operated. This contact results in knife blade 40 becoming embedded in and thus integral with knife ring 36. Knife blade 40 is then retracted proximally as actuator assembly 14 is released, such that knife ring 36 is removed from anvil assembly 22 thereby disengaging tab members 34. With reference to FIGS. 5 and 5A, knife blade 40 has at least one inwardly swaged portion 41 to facilitate grasping and removal of the knife ring upon retraction of blade 40 from anvil assembly 22. Upon removal of the instrument, anvil ring 18, located on the distal side of the staple line, is impeded by the staple line and slides off body portion 26 as the instrument is withdrawn. Body portion 26, disengaged from anvil ring 18, easily pulls past the staple line since the diameter of body portion 26 is less than the diameter of the staple line. As body portion 26 continues to move proximally, tether line 28, attached at one end to body portion 26 and at the other end to anvil ring 18 at circumferential position 42, pulls on anvil ring 18, rotating anvil ring 18 approximately 90°. Anvil ring 18 is then able to be pulled past the stapled tissue and out of the hollow body organ. By rotating anvil ring 18 approximately 90°, the entire circumferential outer surface 44 need not be put into contact with and stress the stapled tissue upon removal of anvil assembly 22. Rather, in the rotated position, only two small portions of circumferential outer surface 44 need contact the stapled tissue thereby minimizing stretching.

Figure 8:
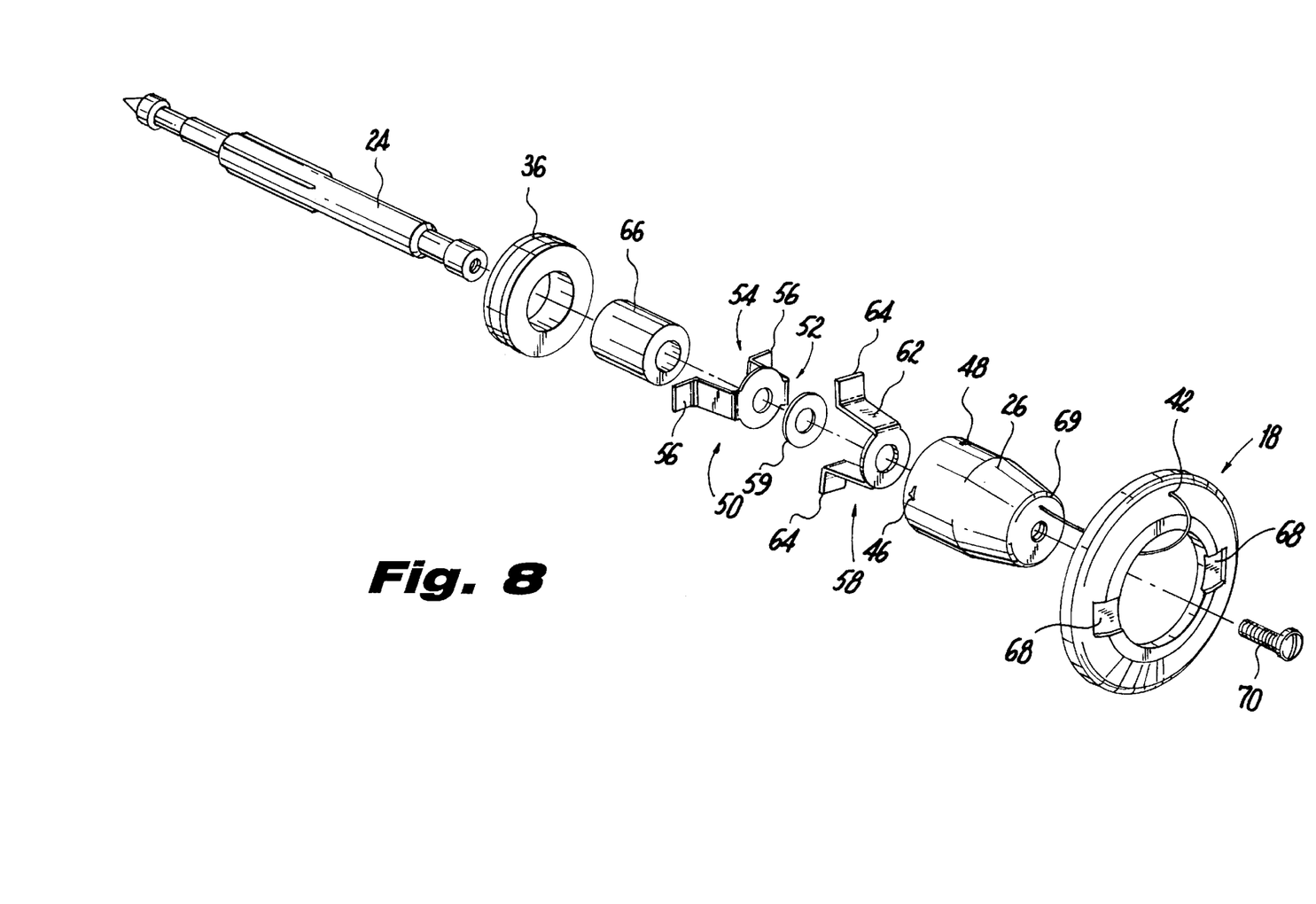
FIG. 8 is an exploded perspective view of another embodiment of an anvil assembly of the present invention.

Referring to FIG. 8, in another embodiment of the present invention, anvil assembly 22a includes anvil body portion 26 having bore 69 therethrough. Body portion 26 further includes two first leg holes 46 (only one shown) and two second leg holes 48 (only one shown) therethrough. Anvil ring 18 is disposed around body portion 26 and is linked to anvil body portion 18 via tether line 28 and includes first leg recesses 68, which will be described below. A first retaining washer 50, having an upper portion 52, and a lower portion 54 forming two leg portions 56, and a second retaining washer 58, having an upper portion 60, and a lower portion 62 forming two leg portions 64, are configured for placement within body portion 26. Spacing washer 59 is disposed between retaining washers 50, 58. Knife ring 36, disposed around spacer 66 and an anvil support rod 24, provides outward biasing pressure against washer leg portions 56 and 64 of first and second retaining washers 50 and 58, respectively, when the anvil assembly 22a is assembled. The biasing pressure forces washer leg portions 56 through first leg holes 46 (only one of two shown), and into first leg recesses 68 thereby engaging body portion 26 with anvil ring 18. The biasing pressure also forces washer leg portions 64 of second washer 58 through second leg holes 48 (only one of two shown) securing anvil body portion 26. Bolt 70 is inserted into bore 69, through the above described elements and into the distal end of anvil support rod 24, thereby fastening the elements together. Anvil assembly 22a can be connected to stapling assembly 12, as shown in FIGS. 1 and 2.

In operation, in a manner similar to that described above with respect to FIGS. 5–7, knife blade 40 (not shown) is directed distally over anvil support rod 24 and into knife ring 36. This contact results in knife blade 40 becoming embedded in and thus integral with knife ring 36. Knife blade 40 is then retracted proximally such that knife ring 36 is removed from contact with leg portions 56 and 64. In the absence of the biasing pressure from knife ring 36, leg portions 64 of second retaining washer 58 remain engaged with body portion 26. Leg portions 56 of first retaining washer 50, however, assume a relaxed position and flex inwardly out of engagement with first leg recesses 68 of anvil ring 18 while remaining secured to body portion 26. Anvil ring 18, located on the distal side of the staple line, is unable to pass through the staple line and is popped off body portion 26 as the instrument is withdrawn through the lumen, thus disengaging anvil ring 18 from body portion 26. Body portion 26, disengaged from anvil ring 18, is pulled past the staple line through the lumen. As body portion 26 continues to move proximally, tether line 28, attached to body portion 26 at circumferential position 42, pulls anvil ring 18, rotating anvil ring 18 approximately 90°. Anvil ring 18 is then able to be pulled past the stapled tissue and out of the hollow body organ in a manner which minimizes contact of circumferential outer surface 44 with the stapled tissue.

Figure 9:
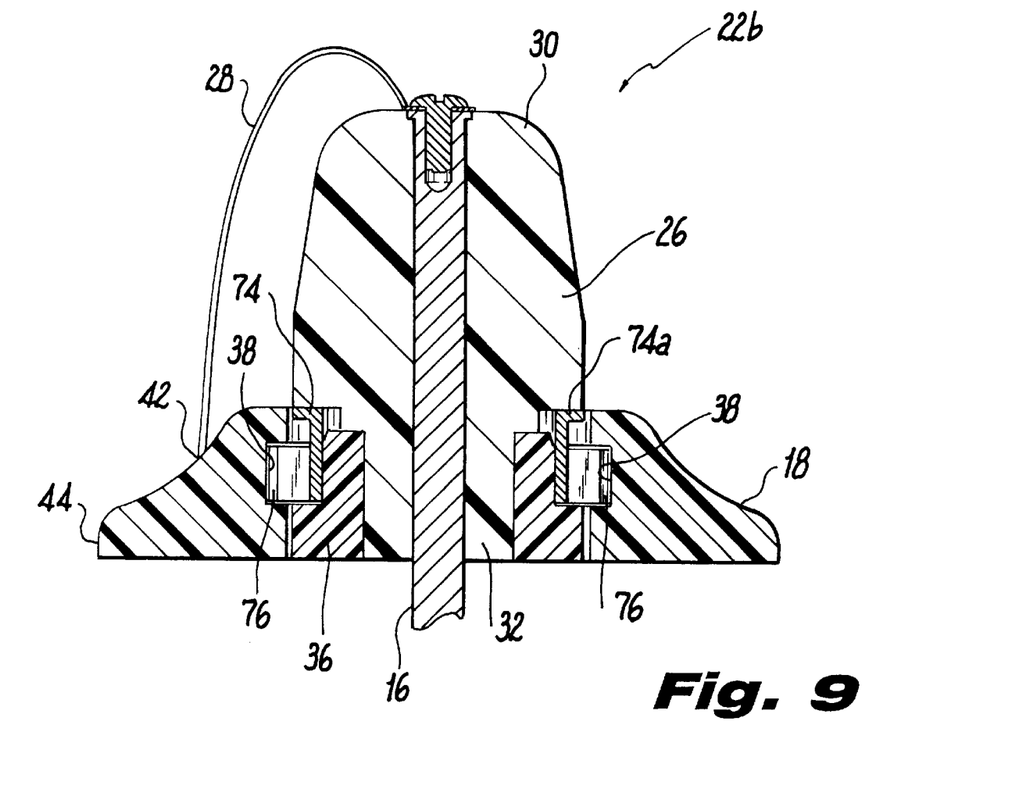
FIG. 9 is a partial cross-sectional view of a further embodiment of an anvil assembly of the present invention.
Figure 9A:
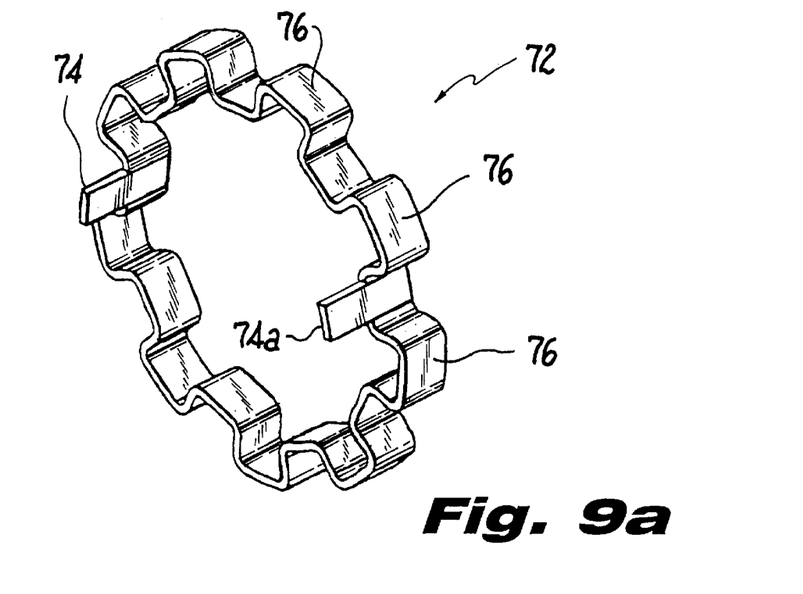
FIG. 9a is a perspective view of a corrugated spring band utilized with the anvil assembly of FIG. 9.

Referring to FIGS. 9 and 9a, another embodiment of the present invention, utilizes corrugated spring band 72 configured for placement within body portion 26 to secure anvil ring 18 to body portion 26. Anvil assembly 22b includes spring band 72, attached to anvil body portion 26 via flexible members 74 and 74a such that flexible members 74 and 74a flex from a straight configuration (FIG. 9a) to a substantially angled configuration (FIG. 9) that defines a plurality of male members 76. Knife ring 36 placed within spring band 72 provides biasing pressure against spring band 72 in an outward direction towards anvil ring recesses 38, expanding spring band 72 such that male members 76 are placed within recesses 38 thereby retaining anvil ring 18 with body portion 26.

In operation, in a manner similar to that described above with respect to FIGS. 5–7, knife blade 40 is directed distally over anvil support rod 24 (not shown) and into contact with knife ring 36 causing knife blade 40 to become embedded in and thus integral with knife ring 36. Knife blade 40 and knife ring 36 are then moved proximally removing knife ring 36 from within spring band 72. Absent biasing pressure from knife ring 36, male members 76 of spring band 72 are allowed to move inwardly from recesses 38. As the instrument is removed, anvil ring 18, located on the distal side of the staple line, is unable to pass through the staple line and is popped off body portion 26 thus disengaging anvil ring 18 from body portion 26. Body portion 26, disengaged from anvil ring 18, is pulled past the staple line through the lumen. As body portion 26 continues to move proximally, anvil ring 18 is rotated approximately 90° when pulled by tether line 28. Anvil ring 18 in its rotated position, minimizes the contact of circumferential outer surface 44 with stapled tissue as it is pulled past the stapled tissue.

Figure 10:
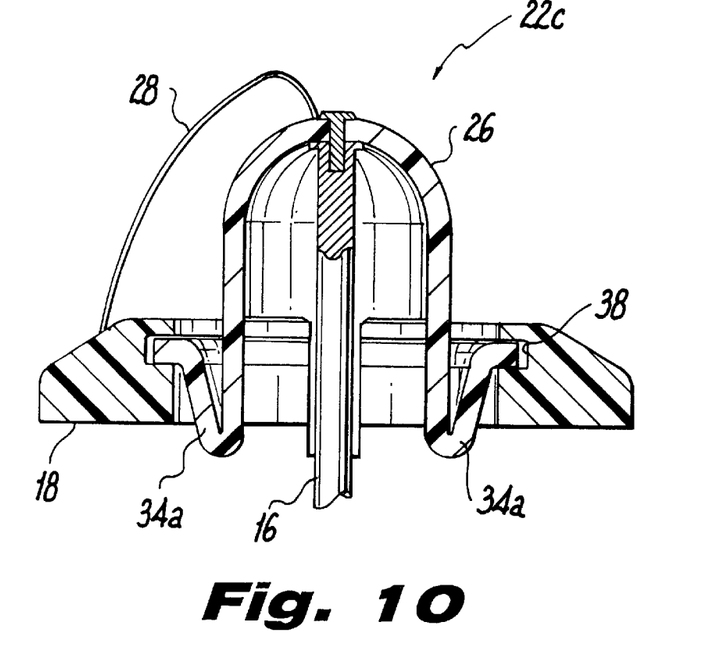
FIG. 10 is a cross-sectional view of another embodiment of an anvil assembly of the present invention.
Figure 11:
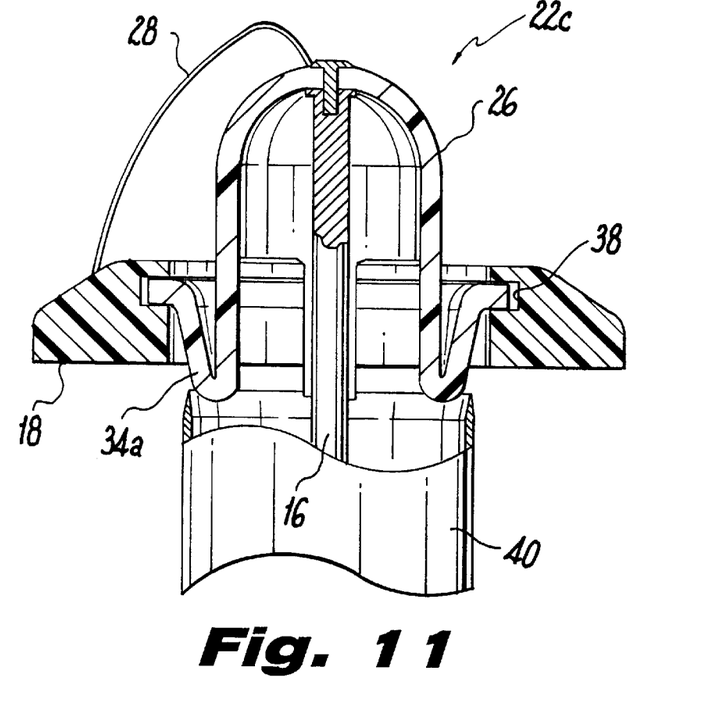
FIG. 11 is a view similar to FIG. 10 illustrating contact of a knife blade with the anvil assembly.
Figure 12:
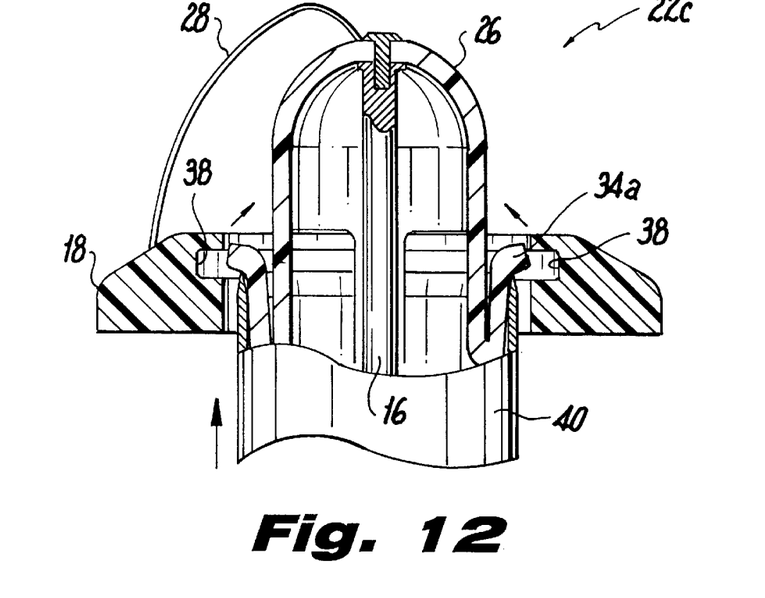
FIG. 12 is a view similar to FIGS. 10-11 with the anvil ring disengaged.
Figure 13:
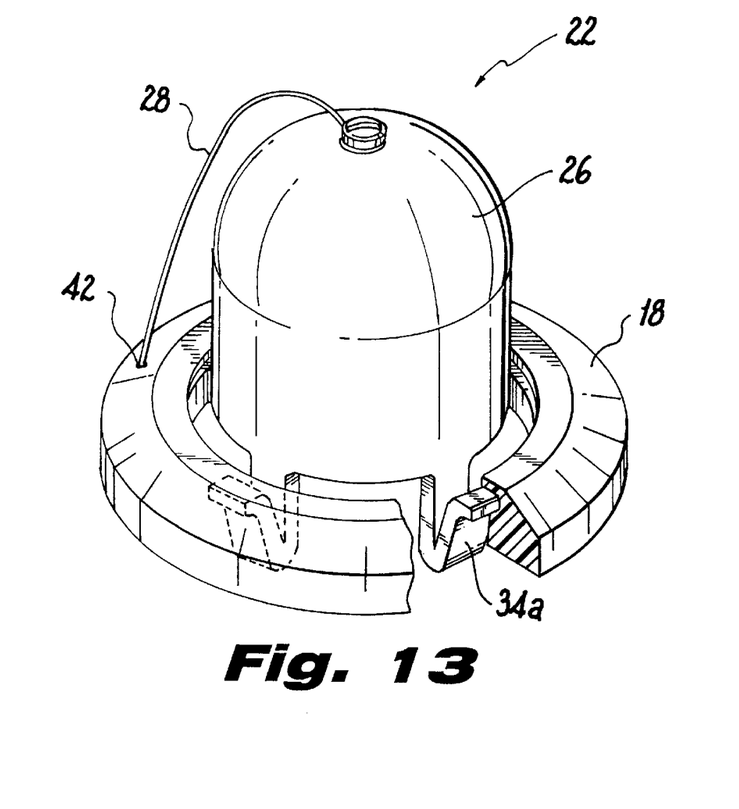
FIG. 13 is a perspective view of the anvil assembly of FIG. 10.

Referring to FIGS. 10–13, another embodiment of the present invention is shown. Anvil assembly 22c includes anvil ring 18 disposed around body portion 26 and connected to body portion 26 via tether line 28. Anvil body portion 26 has tab members 34a which are configured for placement within recesses 38 of anvil ring 18. Referring to FIG. 10, at a resting, outwardly biased position, tab members 34a are positioned within recesses 38 of anvil ring 18. In operation, in a manner similar to that described above with respect to FIGS. 5–7, knife blade 40 is directed distally into contact with tab members 34a as shown in FIG. 11. As knife blade 40 is further moved distally, knife blade 40 provides biasing pressure against tab members 34a in an inward direction away from recesses 38. The biasing pressure forces tab member 34a inward and out of engagement with recesses 38 as shown in FIG. 12. As the instrument is removed, anvil ring 18, located on the distal side of the staple line, is unable to pass through the staple line and is popped off body portion 26 thus disengaging anvil ring 18 from body portion 26. Body portion 26, disengaged from anvil ring 18, is pulled past the staple line through the lumen. As body portion 26 continues to move proximally with anvil ring 18 in tow via tether line 28 which is attached to anvil ring 18 at circumferential position 42, anvil ring 18 is rotated approximately 90°. Anvil ring 18 is then pulled past the stapled tissue and out of the hollow body organ. Once again, by rotating anvil ring 18 approximately 90°, the entire circumferential outer surface 44 of anvil ring 18 need not be put into contact with the stapled tissue during the removal of anvil ring 18 from the hollow body organ.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. An anvil assembly for use with a circular stapling device, said anvil assembly comprises:

(a) an anvil support member having a proximal end and a distal end, the proximal end of the anvil support member engageable with the circular stapling device;

(b) a body portion mounted on the distal end of the anvil support member;

(c) a monolithically formed anvil portion disengageable from said body portion;

(d) means for latching said anvil portion to said body portion, said latching means having at least one male member associated with said body portion for engaging said anvil portion, said anvil portion having at least one recess for engaging said latching means;

(e) a tether line having a first end affixed to said body portion and a second end affixed to said anvil portion for linking said body portion to said anvil portion when said anvil portion is disengaged from said body portion; and (f) biasing means associated with said latching means, said biasing means configured to provide biasing pressure against said at least one made member for positioning said at least one male member into said at least one recess thereby latching said anvil portion with said body portion, said biasing means having a knife ring positioned within said body portion, said knife ring being removable upon engagement with a knife blade of said circular stapling device during operation of said device.

2. An anvil assembly for use with a circular stapling device, said anvil assembly comprises:

(a) an anvil support member having a proximal end and a distal end, the proximal end of the anvil support member engageable with the circular stapling device;

(b) a body portion mounted on the distal end of the anvil support member;

(c) a monolithically formed anvil portion disengageable from said body portion;

(d) means for latching said anvil portion to said body portion, said latching means having a corrugated spring band associated with said body portion defining a plurality of male members for engaging said anvil portion;

(e) a tether line having a first end affixed to said body portion and a second end affixed to said anvil portion for linking said body portion to said anvil portion when said anvil portion is disengaged from said body portion; and (f) a knife ring positioned within said body portion, said knife ring being removable upon engagement with a knife blade of said circular stapling device during operation of said device.

3. An anvil assembly for use with a circular stapling device, said anvil assembly comprises:

(a) an anvil support member having a proximal end and a distal end, the proximal end of the anvil support member engageable with the circular stapling device;

(b) a body portion mounted on the distal end of the anvil support member;

(c) a monolithically formed anvil portion disengageable from said body portion;

(d) means for latching said anvil portion to said body portion, said latching means having a washer assembly having at least one washer, said at least one washer secured to said body portion and having at least one leg portion configured for placement into a recess in said anvil portion;

(e) a tether line having a first end affixed to said body portion and a second end affixed to said anvil portion for linking said body portion to said anvil portion when said anvil portion is disengaged from said body portion; and (f) biasing means for biasing said at least one washer leg portion into said anvil portion recess, said biasing means including a knife ring positioned within said body portion, said knife ring being removable upon engagement with a knife blade of said circular stapling device during operation of said device.

4. An anvil assembly for use with a circular stapling device, said anvil assembly comprises:

(a) an anvil member having an annular array of staple-clinching grooves, said anvil member further having at least one radial recess on an inner surface of said anvil member;

(b) an anvil body engageable with said anvil member, said anvil body having an upper portion and a lower portion, said anvil body lower portion having at least one radially outwardly directed protrusion adapted to engage said at least one radial recess of said anvil member;

(c) a biasing member for biasing said at least one radially outwardly directed protrusion into said at least one radial recess; and (d) a tether line for linking said anvil body with said anvil member having a first end affixed to said upper portion of said anvil body, and a second end affixed to said anvil member.

5. An anvil assembly for use with a circular stapling device having a handle assembly at a proximal end and a staple carrying portion at a distal end, the anvil assembly comprising:

(a) a body portion engagable with the staple carrying portion of the circular stapling device;

(b) a monolithically formed anvil portion disengageable from said body portion;

(c) a washer assembly having at least one washer, said at least one washer secured to said body portion and having at least one leg portion configured for placement into a recess in said anvil portion; and (d) means for linking said body portion to said anvil portion when said anvil portion is disengaged from said body portion.

6. An anvil assembly for use with a circular stapling device, said anvil assembly comprises:

(a) an anvil member having an annular array of staple-clinching grooves, said anvil member further having a plurality of recesses;

(b) an anvil body mounted on an anvil support member, the anvil body engageable with said anvil member, the anvil body having an upper portion, and a lower portion, forming a plurality of leg portions, said leg portions defining a plurality of latch members for placement into said recesses of said anvil member;

(c) a biasing member for biasing said latch members into said recesses; and (d) a tether line for linking said anvil body with said anvil member having a first end affixed to said upper portion of said anvil body, and a second end affixed to said anvil member.

7. The anvil assembly of claim 6 wherein said biasing member is a knife ring removable upon engagement with a knife blade of the circular stapling device during operation of the device.

8. An anvil assembly for use with a circular stapling device, said anvil assembly comprises:

(a) a body portion;

(b) a monolithically formed anvil portion disengageable from said body portion, said anvil portion having at least one recess for engaging a latching mechanism;

(c) a latching mechanism having at least one male member associated with said body portion for engaging said at least one recess of said anvil portion and releasably securing said anvil portion to said body portion;

(d) means for linking said body portion to said anvil portion when said anvil portion is disengaged from said body portion; and (e) biasing means associated with said latching mechanism, said biasing means configured to provide biasing pressure against said at least one male member for positioning said at least one male member into said at least one recess thereby releasably securing said anvil portion to said body portion.

9. The anvil assembly of claim 8 wherein said biasing means is a knife ring positioned within said body portion, said knife ring being removable upon engagement with a knife blade of said circular stapling device during operation of said device.

10. An anvil assembly for use with a circular stapling device, said anvil assembly comprises:

(a) an anvil support member having a proximal end and a distal end, the proximal end of the anvil support member engageable with the circular stapling device;

(b) a body portion mounted on the distal end of the anvil support member;

(c) a monolithically formed anvil portion disengageable from said body portion;

(d) means for latching said anvil portion to said body portion; and (e) a tether fine having a first end affixed to said body portion and a second end affixed to said anvil portion for linking said body portion to said anvil portion when said anvil portion is disengaged from said body portion wherein said latching means is at least one tab member extending from said body portion for engagement with at least one recess in said anvil portion, said at least one tab member being movable from an engaged position to a disengaged position by contact with a knife blade of said circular stapling device during operation of said device, thereby removing said at least one tab member from said at least one recess to disengage said anvil portion from anvil body portion.

11. The anvil assembly of claim 10 further comprising a removable knife ring positioned within said body portion, said knife blade being embedded in said ring during at least part of the operation of said device.

12. The anvil assembly of claim 10 wherein said anvil portion further comprises an annular array of staple-clinching grooves.

13. An anvil assembly for use with a circular stapling device, said anvil assembly comprises:

(a) an anvil body portion having an anvil support member extending therefrom and engageable with the circular stapling device the anvil body portion having at least one tab member extending outwardly therefrom;

(b) an anvil ring member disengageable from said anvil body portion and having an annular array of staple-clinching grooves, said anvil ring member further having at least one recess adapted to receive said at least one tab member of said body portion thereby engaging said anvil ring member to said anvil body portion;

(c) removable biasing means disposed within said body portion for maintaining said at least one tab member within said at least one recess; and (d) means for linking said anvil ring member and said anvil body portion when said anvil ring member is disengaged from said anvil body portion.

14. The anvil assembly of claim 13 wherein said linking means is a tether line having a first end affixed to said anvil body portion, and a second end affixed to said anvil ring member.

15. The anvil assembly of claim 13 wherein said biasing means is a knife ring removable upon engagement with a knife blade of said circular stapling device during operation of said device with said knife blade.

* * * * *